United States Patent [19]
de Agudelo et al.

[11] Patent Number: 5,880,324
[45] Date of Patent: Mar. 9, 1999

[54] CATALYST FOR USE IN THE DEHYDROGENATION AND ISOMERIZATION OF PARAFFINS AND METHOD

[75] Inventors: Maria Magdalena de Agudelo; Trino Romero; Jose Guaregua; Marisela Gonzalez, all of Caracas, Venezuela

[73] Assignee: Intevep, S.A., Caracas, Venezuela

[21] Appl. No.: 102,693

[22] Filed: Jun. 22, 1998

Related U.S. Application Data

[62] Division of Ser. No. 902,186, Jul. 29, 1997, Pat. No. 5,821,188, which is a continuation of Ser. No. 544,606, Nov. 6, 1995, Pat. No. 5,658,839, which is a division of Ser. No. 353,812, Dec. 12, 1994, abandoned, which is a division of Ser. No. 181,770, Jan. 21, 1994, Pat. No. 5,416,052.

[51] Int. Cl.$^6$ ...................................................... C07C 5/13
[52] U.S. Cl. ........................... 585/739; 208/136; 208/138
[58] Field of Search .............................. 585/739; 208/138, 208/136

[56] References Cited

U.S. PATENT DOCUMENTS 5,242,576  9/1993  Schmidt et al. ........................... 208/78

*Primary Examiner*—Gary P. Straub
*Assistant Examiner*—Thomas G. Dunn, Jr.
*Attorney, Agent, or Firm*—Bachman & LaPointe, P.C.

[57] ABSTRACT

A catalyst comprising a modified mordenite zeolite catalyst modified with Pt and a promoter selected from the group consisting of Group IIB, Group IVA, Group VIB and mixtures thereof is effectively used in a process for the simultaneous dehydrogenation and isomerization of paraffins to isoparaffins and isoolefins under controlled conditions. The catalyst is prepared by depositing on the modified mordenite zeolite catalyst sequentially Pt and thereafter the promoter.

3 Claims, No Drawings

CATALYST FOR USE IN THE DEHYDROGENATION AND ISOMERIZATION OF PARAFFINS AND METHOD

CROSS-REFERENCE TO RELATED APPLICATIONS

This application is a divisional of application Ser. No. 08/902,186 filed Jul. 29, 1997, now U.S. Pat. No. 5,821,188, which is a continuation of application Ser. No. 08/554,606 filed Nov. 6, 1995, now U.S. Pat. No. 5,658,839, which in turn is a divisional of application Ser. No. 08/353,812 filed Dec. 12, 1994, now abandoned, which in turn is a divisional of application Ser. No. 08/181,770 filed Jan. 21, 1994, now U.S. Pat. No. 5,416,052.

BACKGROUND OF THE INVENTION

The present invention relates to a catalyst for use in a process for the simultaneous dehydrogenation and isomerization of paraffins to isoparaffins and isoolefins and method for preparing the catalyst and, more particularly, a modified mordenite zeolite catalyst containing Pt and a promoter.

Various processes exist in the prior art for converting paraffins to dehydrogenated and isomerized products. The dehydrogenated and isomerized products are particularly useful for the production of high demand products such as methyl, tertiary butyl ether (MTBE) and isobutylenes.

Heretofore the processes for dehydrogenation and isomerization of hydrocarbons have been developed independently following different paths. Dehydrogenation processes known in the art for the past 25 years have employed catalysts which comprise a noble metal, usually Pt, supported on a non-acid support, typically alumina or silica alumina. It is known in the prior art to further modify such a catalyst with one or two promoters so as to control the cracking of the hydrocarbon feedstock being subjected to the dehydrogenation process. Examples of catalysts of the type mentioned above are disclosed in U.S. Pat. Nos. 3,679,773; 4,000,210; and 4,177,218. Over the past ten years it has been the tendency in the prior art to increase the number of promoters used in noble metal catalysts so as to further reduce the loss of feedstock due to catalytic cracking. This tendency is clearly demonstrated in U.S. Pat. Nos. 4,381, 257; 4,486,547; 4,880,764; and 5,012,027. The most commonly used promoters in the prior art discussed above have been selected from Groups IVA, VIB and VIII of the Periodic Table. These known prior art catalysts exhibit high activity, selectivity and stability for the hydrogenation of straight chain paraffins to straight chain olefins. The paraffin isomerization processes known in the prior art have generally been based on catalysts comprising noble metals supported on an alumina matrix and modified with chlorine, fluorene and ammonium. Examples of such catalysts are shown in U.S. Pat. Nos. 3,442,794 and 4,489,216. Recently, the prior art has employed zeolite supports in place of the alumina supports noted above. Zeolites, and particularly mordenite, have been used extensively due to the fact that they present no corrosion problems and have a high resistance to sulfur contained in the hydrocarbon feedstock. Examples of such catalysts are shown in U.S. Pat. Nos. 3,507,931; 3,551,353; 3,932,554; 4,400,576; 4,935,578; and 5,132,479. Further approaches have been tried for the isomerization of hydrocarbons using non-zeolite molecular sieves such as silica alumina phosphates as described in U.S. Pat. No. 5,132,484. All of the catalysts described above exhibit high activity, selectivity, and stability for the isomerization reaction while minimizing possible side reactions.

While the prior art discussed above have developed processes for the dehydrogenation of hydrocarbons and processes for the isomerization of hydrocarbons, few processes have been developed which are capable of the simultaneous isomerization and dehydrogenation of paraffin feedstocks to isoparaffins and isoolefins. The only process known to the inventors which is capable of simultaneous isomerization and dehydrogenation is described in U.S. Pat. No. 4,962,266 to Shum. The process described in the '266 patent employs a Pt based catalyst with zinc silicates. The drawback of the process of the '266 patent is loss of paraffins to side reactions which makes the process unattractive on a commercial basis.

Naturally, it would be highly desirable to provide an improved catalyst for the simultaneous dehydrogenation and isomerization of paraffins to isoparaffins and isoolefins wherein paraffin side reactions are limited.

Accordingly, it is the principal object of the present invention to provide a catalyst for the simultaneous dehydrogenation and isomerization of paraffins to isoparaffins and isoolefins. It is a further object of the present invention to provide a method for preparing a catalyst for use in the simultaneous hydrogenation and isomerization of paraffins to isoparaffins and isoolefins.

It is a still further object of the present invention to provide a process for the simultaneous dehydrogenation and isomerization of paraffins to isoparaffins and isoolefins employing a single catalyst.

Further objects and advantages of the present invention will appear hereinbelow.

SUMMARY OF THE INVENTION

The present invention relates to a catalyst for use in a process for the simultaneous dehydrogenation and isomerization of paraffins and a method for preparing the catalyst and, more particularly, a modified mordenite zeolite catalyst containing Pt and a promoter.

The catalyst according to the present invention comprises a mordenite zeolite catalyst containing Pt and a promoter selected from the group consisting Group IIB, Group IVA, Group VIB and mixtures thereof. The mordenite zeolite catalyst is preferably a mordenite H zeolite catalyst having a Si:Al ratio of about between 5:1 to 50:1. The Pt and promoter are both present in the final catalyst each in an amount of about between 0.1 to 1.5% by weight. In accordance with a preferred embodiment of the present invention, the promoter is selected from the group consisting Zn, Sn, Cr and mixtures thereof.

The method for preparing the catalyst of the present invention as described above comprises modifying a mordenite zeolite catalyst with Pt and a promoter. The method of the present invention comprises providing a mordenite zeolite catalyst and modifying the mordenite zeolite catalyst by incorporating Pt into the mordenite zeolite catalyst. After the Pt has been incorporated into the mordenite zeolite catalyst, the Pt modified mordenite catalyst is further modified by incorporating a promoter selected from the group consisting of Group IIB, Group IVA, Group VIB and mixtures thereof. The Pt and promoter may be incorporated into the mordenite zeolite catalyst by either impregnation or by ion exchange. The preferred embodiment for incorporating the Pt and promoter is incorporation by impregnation and comprises the steps of impregnating the mordenite zeolite catalyst with a Pt salt aqueous solution of desired concentration, drying and calcining the Pt impregnated mordenite zeolite catalyst and thereafter reducing the Pt impregnated catalyst in the presence of hydrogen to convert substantially all of the Pt to metallic form. Thereafter, the Pt impregnated catalyst is further impregnated with a promoter salt aqueous solution of desired concentration and the promoter impregnated catalyst is thereafter oxidized so as to oxidize the promoter.

The process of the invention for the simultaneous dehydrogenation and isomerization of paraffins to isoparaffins and isoolefins comprises the steps of providing a reactor and locating the mordenite zeolite catalyst containing Pt and a promoter in the reactor. Thereafter the catalyst is activated in situ in the presence of hydrogen at elevated temperatures. The catalyst is thereafter contacted with the paraffin in the reactor in the presence of hydrogen under the following conditions: a paraffin space velocity of about between 0.1 to 1000h$^{-1}$, a hydrogen to paraffin ratio of about between 0.1 to 30; and a temperature of about between 250° to 800° C. The products produced by the process of the present invention are particularly useful for producing MTBE.

DETAILED DESCRIPTION

The catalyst of the present invention for use in the simultaneous dehydrogenation and isomerization of paraffins to isoparaffins and isoolefins comprises a mordenite zeolite catalyst which is modified with Pt and a promoter selected from the group consisting of Group IIB, Group IVA, Group VIB and mixtures thereof. The preferred mordenite zeolite catalyst is a mordenite H zeolite catalyst having a Si:Al ratio of about between 5:1 to 50:1. The Si:Al ratio is chosen so as to control the acidity of the mordenite H zeolite catalyst. By regulating the acidity of the mordenite H zeolite catalyst the ability to crack paraffins is reduced while at the same the ability to isomerize the paraffins is increased. The modified mordenite H zeolite catalyst of the present invention contains platinum in the final catalyst structure in an amount of about between 0.1 to 1.5% by weight and the promoter in an amount of about between 0.1 to 1.5% by weight. The preferred promoters used in the catalyst of the present invention are Zn, Sn, Cr and mixtures thereof.

In accordance with the method for preparing the catalyst in accordance with the present invention, the Pt and promoter may be incorporated into the mordenite zeolite catalyst by impregnation or by ion-exchange. The preferred method of the present invention for preparing the catalyst includes the steps of firstly incorporating Pt into the zeolite catalyst and thereafter modifying the Pt modified mordenite zeolite catalyst by incorporating therein the promoter. It is a critical feature of the present invention that the platinum be incorporated into the mordenite zeolite catalyst prior to the incorporation of the promoter. In accordance with the preferred feature of the present invention, the platinum impregnated mordenite catalyst is reduced in the presence of hydrogen so as to convert substantially all of the Pt to metallic form prior to impregnating the modified mordenite zeolite catalyst with the promoter salt. By reducing the Pt prior to incorporation of the promoter into the catalyst, it has been found that cracking of the paraffin feedstock is reduced during the dehydrogenation and isomerization of the paraffin feedstock. Again, it is critical in the present invention when preparing the catalyst to incorporate the platinum first prior to incorporation of the promoter as this sequence results in a catalyst which has a higher selectivity for isomerization and dehydrogenation. After incorporating the promoter into the Pt modified mordenite zeolite catalyst, the catalyst is oxidized so as to oxidize the promoter so as to produce a bifunctional catalyst suitable for simultaneous dehydrogenation and isomerization of paraffins. The preferred method for producing the catalyst of the present invention comprises incorporating the mordenite zeolite catalyst with the Pt and promoter by impregnation. The mordenite zeolite catalyst is first impregnated with a Pt salt aqueous solution of a concentration sufficient to yield a final catalyst having a Pt content of about between 0.5 to 1.5% by weight. Particularly suitable Pt salts are those selected from the group consisting of Pt(NH$_3$)$_4$Cl$_2$, Pt(NH$_3$)$_4$Cl$_3$, Pt(NO$_3$)$_4$(NO$_3$)$_2$ and mixtures thereof. The Pt impregnated mordenite zeolite catalyst is thereafter dried at a temperature of about between 60° to 200° C. and calcined at a temperature of about between 200° to 600° C. The dried and calcined Pt modified mordenite zeolite catalyst is thereafter reduced in a hydrogen environment at a temperature of about between 200° to 700° C. for sufficient time to insure that the Pt is reduced to metallic form. The reduced Pt impregnated catalyst is thereafter impregnated with a promoter salt aqueous solution of desired concentration so as to yield a catalyst having a promoter concentration of about between 0.5 to 1.5% by weight in the final catalyst structure. The catalyst is thereafter dried and calcined at a temperature of about between 200° to 600° C. so as to oxidize the promoter. The resulting catalyst is a bifunctional catalyst suitable for the simultaneous dehydrogenation and isomerization of paraffins.

The process for the simultaneous dehydrogenation and isomerization of paraffins to isoparaffins and isoolefins comprises the steps of locating the catalyst of the present invention modified with Pt and the promoter in a reactor and activating the catalyst under the following conditions prior to contacting the catalyst with a paraffin feedstock: in a hydrogen environment at a temperature of about between 200° to 800° C. for at least one hour. The activated catalyst is thereafter contacted with the paraffinic feedstock in the presence of hydrogen under the following conditions: (1) a paraffin space velocity of about between 0.1 to 1000h$^{-1}$; (2) a hydrogen to paraffin ratio of about between 0.1 to 30; and a temperature of about between 250° to 800° C. In accordance with the preferred embodiment of the process of the present invention the paraffins are fed to the catalyst with a space velocity of about between 0.1 to 250h$^{-1}$, a hydrogen to paraffin ratio of about between 1 to 15 and a temperature of about between 500° to 600° C. The process of the present invention allows for the effective simultaneous dehydrogenation and isomerization of paraffins to isoparaffins and isoolefins while greatly reducing the cracking of the paraffins.

The advantages of the present invention will be made clear from a consideration of the following illustrative examples.

EXAMPLE 1

A catalyst in accordance with the present invention, catalyst A, was prepared as follows. A mordenite zeolite catalyst having a Si:Al ratio of 10 to 1 was impregnated with a solution of tetramoniumplatinum nitrate. The Pt impregnated mordenite was thereafter dried at a temperature of 120° C. for 6 hours and calcined at a temperature of 500° C. for 12 hours. The zeolite Pt modified mordenite was thereafter impregnated with a solution of zinc nitrate, dried at 120° C. for 6 hours and calcined at 500° C. for 12 hours so as to obtain a final catalyst structure having the following chemical and physical properties.

TABLE 1

| Catalyst A | |
| --- | --- |
| Pt | 0.47% by wt. |
| Zn | 1.10% by wt. |
| Na | 0.20% by wt. |
| Al | 4.10% by wt. |
| Si | 41.00% by wt. |
| Total surface area | 491 ($M^2/g$) |

Catalyst A was thereafter employed in a reactor for the simultaneous dehydrogenation and isomerization of a paraffin feedstock. The catalyst was first activated in a hydrogen environment for 1 hour at a temperature of 550° C. An n-butane feedstock was then fed to the reactor at a liquid space velocity of $90h^{-1}$ in the presence of hydrogen. The ratio of $H_2$ to the n-butane feedstock was 5. Reaction temperature in the reactor was 550° C. 30% of the n-butane was converted and the conversion products obtained are set forth below in Table 2.

TABLE 2

| Products (mol %) | |
| --- | --- |
| $C_1 + C_2 + C_3$ | 15.0 |
| Isobutane | 7.3 |
| Isobutene | 18.3 |
| 1-butene | 15.5 |
| Trans-2 butene | 25.6 |
| Cis-2-butene | 18.5 |

EXAMPLE 2

In order to demonstrate the criticality for reducing the Pt impregnated mordenite zeolite prior to impregnation with the promoter, a second catalyst, catalyst B, was prepared under the same conditions as Example 1 above with the exception that, after incorporation of the Pt into the mordenite zeolite the Pt impregnated mordenite was reduced in the presence of hydrogen for 2 hours at a temperature of 350° C. The composition of the final catalyst B was identical to that of catalyst A of Example 1. Catalyst B was then employed in the dehydrogenation and isomerization process of the present invention for converting n-butane under the same conditions as catalyst A in Example 1. The conversion of n-butane was 45% and the conversion process products obtained are set forth below in Table 3.

TABLE 3

| Products (mol %) | |
| --- | --- |
| $C_1 + C_2 + C_3$ | 6.0 |
| Isobutane | 10.0 |
| Isobutene | 13.0 |
| 1-butene | 24.8 |

TABLE 3-continued

| Products (mol %) | |
| --- | --- |
| Trans-2 butene | 29.0 |
| Cis-2-butene | 18.0 |

It can clearly be seen that by reducing the Pt modified mordenite prior to impregnation with the promoter greater conversion of the n-butane is obtained along with higher quality conversion products. Table 4 below compares the selectivity and conversion for catalysts A and B.

TABLE 4

| Catalyst | A | B |
| --- | --- | --- |
| % Conversion | 30.0 | 45.0 |
| Selectivity | | |
| % Cracking | 15.0 | 6.0 |
| % Isomerization | 7.3 | 10.0 |
| % Dehydrogenation | 77.7 | 84.0 |

EXAMPLE 3

In order to demonstrate the effect of the hydrogen feedstock ratio on the process of the present invention for the simultaneous dehydrogenation and isomerization of paraffins, catalyst B of Example 2 was used to convert n-butane under 3 different hydrogen to feedstock ratios at 550° C. The results are set forth below in Table 5.

TABLE 5

| $H_2/n-C_4$ | 3 | 5 | 10 |
| --- | --- | --- | --- |
| % Conversion | 37.6 | 44.3 | 48.6 |
| Products (mol %) | | | |
| $C_1 + C_2 + C_3$ | 0 | 6.0 | 33.0 |
| Isobutane | 0 | 10.0 | 17.0 |
| Isobutene | 9.0 | 13.0 | 12.6 |
| 1-butene | 31.9 | 24.8 | 13.6 |
| Trans-2-butene | 36.7 | 29.0 | 13.0 |
| Cis-2-butene | 22.7 | 18.0 | 10.8 |

As can be seen from Table 5, as the ratio of $H_2$ to feedstock increases, so does the percent conversion increase. However, product quality decreases.

EXAMPLE 4

In order to demonstrate the criticality of impregnation of Pt prior to the incorporation of the promoter, a third catalyst, catalyst C, was prepared as discussed above in Example 1 wherein Zn was incorporated first, prior to Pt incorporation and used to treat an n-butane feedstock under the following conditions: a hydrogen to butane ratio of 10 at a processing temperature of 550° C. The results are indicated herein below.

TABLE 6

| Catalyst | A | C |
| --- | --- | --- |
| % Conversion | 30.0 | 37.0 |
| Selectivity | | |
| % Cracking | 15.0 | 32.1 |

TABLE 6-continued

| Catalyst | A | C |
|---|---|---|
| % Isomerization | 7.3 | 4.0 |
| % Dehydrogenation | 77.7 | 63.4 |

As can be seen from the above, when the promoter is impregnated into the mordenite zeolite prior to Pt incorporation, the cracking of the paraffin feedstock is increased thereby resulting in a decrease in dehydrogenation and isomerization which is undesirable.

EXAMPLE 5

In order to demonstrate the effect of the promoter in the catalyst of the present invention two additional catalysts, catalysts D and E, were prepared using different concentrations of various promoters. In catalyst D the promoter concentration was 0.5% by weight while in catalyst E the promoter concentration was 1.0% by weight. In catalyst F the promoter was Cr in an amount of 1.0% by weight (Zn). In catalyst G no promoter was employed. The catalysts D, E, F and G were used to convert n-butane under a hydrogen to butane ratio of 10 at a temperature of 550° C. The results are shown in Table 7 below.

TABLE 7

| Catalyst | D | E | F | G |
|---|---|---|---|---|
| Promoter (wt. %) | 0.5Zn | 1.0Zn | 1.0Cr | 0 |
| % Conversion | 40.0 | 30.0 | 30.8 | 45.0 |
| Selectivity | | | | |
| % Cracking | 42.5 | 15.0 | 20.0 | 51.3 |
| % Isomerization | 7.8 | 7.8 | 6.3 | 10.8 |
| % Dehydrogenation | 49.7 | 77.7 | 73.7 | 37.8 |

It can be seen from the foregoing that the percent dehydrogenation increases with an increase in promoter concentration.

Table 8 sets forth the products obtained when processing n-butane with each of the catalysts D, E, F and G.

TABLE 8

| Catalyst | D | E | F | G |
|---|---|---|---|---|
| Products (mol %) | | | | |
| $C_1 + C_2 + C_3$ | 24.5 | 15.0 | 21.0 | 51.0 |
| Isobutane | 6.6 | 7.3 | 6.3 | 10.6 |
| Isobutene | 16.3 | 18.3 | 8.0 | 13.2 |
| 1-butene | 17.5 | 15.5 | 22.0 | 8.5 |
| Trans-2-butene | 20.5 | 25.6 | 23.4 | 10.0 |
| Cis-2-butene | 14.6 | 18.5 | 16.0 | 6.4 |

EXAMPLE 6

This example is to demonstrate the effect of the Si:Al ratio in the catalyst. Catalysts I and J were prepared as shown in Example 1 using mordenite-H with Si:Al ratio of 5 and 10, with Pt concentration of 0.5 wt % and using Zn as a promoter in an amount of 0.5 wt %. The catalysts were used to convert n-butane under a hydrogen to butane ratio of 10 at a temperature of 550° C. The results are shown below in Table 9.

TABLE 9

| Catalyst | I | J |
|---|---|---|
| Si:Al | 5 | 10 |
| % Conversion | 40.0 | 38.0 |
| Products (mol %) | | |
| $C_1 + C_2 + C_3$ | 33.6 | 40.0 |
| Isobutane | 5.0 | 7.8 |
| Isobutene | 2.3 | 15.2 |
| 1-butene | 16.2 | 12.7 |
| Trans-2-butene | 20.7 | 15.2 |
| Cis-2-butene | 22.2 | 9.9 |

EXAMPLE 7

A zeolite of the mordenite-H type, with a Si:Al ratio of 10 is exchanged for 48 hours with a solution of tetraamonium platinum (II) chloride so as to incorporate 0.2% Pt. The exchanged catalyst is dried at 120° C. for 6 hours and dehydrated at 350° C. for 12 hours. The dehydrated Pt/moredenite-H is placed under a hydrogen atmosphere for 2 hours at 350° C. to reduce the Pt to its metallic form. The reduced Pt/mordenite-H is impregnated with a solution of zinc nitrate so as to incorporate 1.0% Zn. The Pt/Zn mordenite-H is dried at 120° C. for 12 hours to obtain the catalyst. The catalyst composition is set forth below in Table 10.

TABLE 10

| | Catalyst H | |
|---|---|---|
| Pt | 0.21% | by wt. |
| Zn | 1.00% | by wt. |
| Na | 0.20% | by wt. |
| Al | 4.10% | by wt. |
| Si | 41.00% | by wt. |

Catalyst H was used to convert n-butane under a hydrogen to butane ratio of 5 at a process temperature of 550° C. in accordance with the present invention. The selectivity and conversion for catalyst H is set forth below in Table 11.

TABLE 11

| | Catalyst H |
|---|---|
| % Converstion | 13.0 |
| Selectivity | |
| % Cracking | 4.7 |
| % Isomerization | 4.1 |
| % Dehydrogenation | 91.2 |

Note that while the Pt content of catalyst H was substantially half of that of catalyst A selectivity was maintained although the % conversion was effected.

This invention may be embodied in other forms or carried out in other ways without departing from the spirit or essential characteristics thereof. The present embodiment is therefore to be considered as in all respects illustrative and not restrictive, the scope of the invention being indicated by the appended claims, and all changes which come within the meaning and range of equivalency are intended to be embraced therein.

We claim:

1. A process for the simultaneous dehydrogenation and isomerization of paraffins to isoparaffins and isoolefins comprising the steps of:

providing a reactor;

locating a mordenite zeolite catalyst comprising a mordenite zeolite catalyst having a Si:Al ratio of about between 5:1 to 10:1, Pt in an amount of about between 0.1 to 1.5% by weight wherein the Pt is present in metallic form and a promoter in an amount of about 0.1 to 1.5% by weight wherein the promoter is selected from the group consisting of Zn, Sn, Cr and mixtures thereof in the reactor;

activating the catalyst; and contacting the catalyst with a paraffin in the reactor in the presence of hydrogen under the following conditions:
 (1) paraffin space velocity of about between 0.1 to $1000^{-1}$;
 (2) a hydrogen to paraffin ratio of about between 0.1 to 30; and
 (3) a temperature of about between 250° to 800° C.

2. A process according to claim 1 including activating the catalyst under the following conditions prior to contacting the catalyst with the paraffin:
 (a) in the presence of hydrogen
 (b) at a temperature of 200° to 800° C.;
 (c) for at least 1 hour.

3. A process according to claim 1 wherein the paraffin is selected from the group consisting of n-butane, n-pentane, isobutane and isopentane.

* * * * *